United States Patent [19]

Nakane et al.

[11] Patent Number: 5,504,095
[45] Date of Patent: Apr. 2, 1996

[54] AMINOBENZOSULTAM DERIVATIVES AS LIPOXYGENASE INHIBITORS

[75] Inventors: Masami Nakane, Nagoya; Kunio Satake; Kazuo Ando, both of Handa; Hiroaki Wakabayashi, Chita, all of Japan

[73] Assignee: Pfizer Inc., New York, N.Y.

[21] Appl. No.: 359,709

[22] Filed: Dec. 20, 1994

Related U.S. Application Data

[63] Continuation of Ser. No. 848,942, filed as PCT/US91/06675, Sept. 18 1991, abandoned.

[30] Foreign Application Priority Data

Sep. 19, 1990 [JP] Japan ............................ 2-249535

[51] Int. Cl.$^6$ ............ A61K 31/41; C07D 285/14; C07D 291/08
[52] U.S. Cl. ............ 514/360; 514/362; 514/338; 544/5; 544/11; 544/48; 544/49; 546/270; 546/271; 548/122; 548/126; 548/207
[58] Field of Search ............ 548/122, 126, 548/207; 514/360, 362, 373, 338; 546/270, 271

[56] References Cited

U.S. PATENT DOCUMENTS

| | | | |
|---|---|---|---|
| 3,177,221 | 4/1965 | Carson et al. | 548/126 |
| 3,303,109 | 2/1967 | Loev | 260/243 |
| 3,539,584 | 11/1970 | Suh et al. | 260/304 |
| 4,835,166 | 5/1989 | Kitaura et al. | 514/339 |
| 4,904,685 | 2/1990 | Kitaura et al. | 514/418 |
| 5,006,541 | 4/1991 | Kitaura et al. | 514/367 |
| 5,036,088 | 7/1991 | Kitaura et al. | 514/375 |

FOREIGN PATENT DOCUMENTS

| | | |
|---|---|---|
| 840443 | 4/1970 | Canada . |
| 61470 | 3/1989 | Japan . |

*Primary Examiner*—P. I. Datlow
*Attorney, Agent, or Firm*—Peter C. Richardson; Gregg C. Benson; James T. Jones

[57] ABSTRACT

Aminobenzosultam derivatives, which are inhibitors of lipoxygenase, having the formula

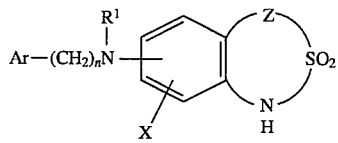

and the pharmaceutically acceptable acid addition salts thereof, wherein Ar is cycloalkyl having five to seven carbon atoms, tetrahydropyranyl, pyridyl, oxazolyl, phenyl or substituted phenyl wherein said substituent is methyl, methoxy, fluoro, chloro or trifluoromethyl; n is an integer of 1 to 3; X is hydrogen, methyl, methoxy, fluoro, chloro or trifluoromethyl; Z is —NH—, —O—, or —CH$_2$—; and R$^1$ is hydrogen or alkyl having one to three carbon atoms.

4 Claims, No Drawings

AMINOBENZOSULTAM DERIVATIVES AS LIPOXYGENASE INHIBITORS

This is a continuation of application Ser. No. 07/848,942, filed on Apr. 21, 1992, now abandoned, with is a National filing under 35 U.S.C. 371 based on [PCT/US91/06675] filed Sep. 18, 1991.

BACKGROUND OF THE INVENTION

This invention relates to novel aminobenzosultam derivatives and their use. The compounds of the present invention inhibit the action of lipoxygenase enzyme and are useful in the treatment or alleviation of inflammatory diseases, allergy and cardiovascular diseases in mammals. This invention also relates to pharmaceutical compositions comprising such compounds.

Arachidonic acid is known to be the biological precursor of several groups of endogenous metabolites, prostaglandins including prostacyclins, thrombaxanes and leukotrienes. The first step of the arachidonic acid metabolism is the release of arachidonic acid and related unsaturated fatty acids from membrane phospholipids, via the action of the phospholipase. Free fatty acids are then metabolized either by cyclooxygenase to produce the prostaglandins and thromboxanes or by lipoxygenase to generate hydroperoxy fatty acids which may be further converted to the leukotrienes.

Leukotrienes have been implicated in the pathophysiology of inflammatory disease, including rheumatoid arthritis, gout, asthma, ischemia reperfusion injury, psoriasis and inflammatory bowel disease. Any drug that inhibits lipoxygenase is expected to provide significant new therapy for both acute and chronic inflammatory conditions.

Recently several review articles on lipoxygenase inhibitors have been reported. (See H. Masamune and L. S. Melvin, Sr., in: Annual Reports in Medicinal Chemistry 24 (1989) pp71–80 (Academic), B. J. Fitzsimmons and J. Rokach in: Leukotrienes and Lipoxygenases (1989) pp 427–502 (Elsevier).

References which relate to benzosultams include U.S. Pat. Nos. 3,539,584, 3,303,190 and 3,177,221, Japanese Patent 4359/68 and Japanese Patent Application (kokai) 61470/89.

SUMMARY OF THE INVENTION

The compounds of the present invention are the formula

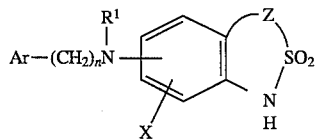

I and the pharmaceutically acceptable acid addition salts there of, wherein Ar is cycloalkyl of five to seven carbon atoms, phenyl, substituted phenyl where said substituent is methyl, methoxy, fluoro, chloro or trifluoromethyl, pyridyl, oxazolyl or tetrahydropyranyl; n is 1 to 3; X is hydrogen, methyl, methoxy, fluoro, chloro or trifluoromethyl; Z is —NH—, —O—, —$CH_2$—, —$OCH_2$—, —$CH_2CH_2$—, —$SCH_2$—, —$CH_2N(CH_3)$—, —$C(CH_3)=N$—, —$CH_2H$—, —$C(O)CH_2$—or —$CN_2N$ ($CH_2$ pyridyl)—; and $R_1$ is hydrogen or alkyl of one to three carbon atoms.

A preferred group of compounds are those wherein Ar is phenyl, $R^1$ is hydrogen and Z is —$CH_2$—. Especially preferred within this group are the compounds 5-N-benzylamino- 1,3-dihydro-2,1-benzisothiazole-2,2-dioxide and 5-N-benzylamino-6-fluoro-1,3-dihydro-2,1-benziso-thiazole- 2,2-dioxide.

A second group of preferred compounds are those wherein Ar is phenyl, X is hydrogen, $R_1$ is hydrogen and Z is —$SCH_2$—, —$OCH_2$—or —$C(O)CH_2$—. Especially preferred within this group are the compounds 7-N-benzylamino-2H,4H- 1,3,4-benzodithiazine-3,3-dioxide, 7-N-benzylamino- 2H,4H-1,3,4-benzothiazine- 3,3-dioxide, 6-N-benzylamino-4-oxo- 3,4-dihydro-1H-2,1-benzothiazine-2,2-dioxide and 7-N-( 3-phenylpropyl)amino-2H,4H-1, 3,4-benzoxathiazine- 3,3dioxide.

A third group of preferred compounds are those wherein Ar is tetrahydropyranyl, n is 1 and $R^1$ is hydrogen. Especially preferred within this group is the compound 7-N-(tetrahydropyran-3-yl)methylamino-2H,4H-1,3,4-benzoxathiazine- 3,3-dioxide.

The present invention also includes a method for treating an allergic or inflammatory condition in a mammal which comprises administering to said mammal an antiallergy or antiinflammatory effective amount of a compound of formula I.

Also included in the present invention is a pharmaceutical composition for the treatment of allergic or inflammatory conditions in a mammal, said composition comprising an effective amount of a compound of formula I with a pharmaceutically acceptable carrier.

The present invention also includes a process for preparing compounds of the formula I, wherein Ar, n, $R^1$, X and Z are as defined, which comprises reducing a compound of the formula

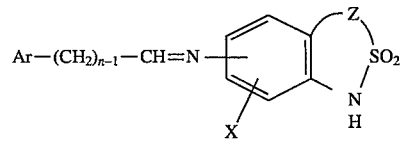

and if desired alkylating those compounds wherein $R^1$ is hydrogen by reductive amination. Especially preferred as reducing agents are sodium borohydride or platinum oxide and hydrogen.

DETAILED DESCRIPTION OF THE INVENTION

The novel compounds of the present invention wherein $R^1$=hydrogen can be prepared by the following synthetic scheme:

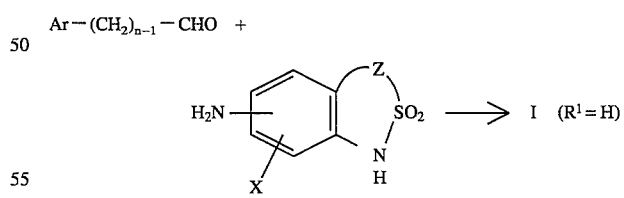

In practice, one mole of the appropriate amino compound is contacted with about a molar equivalent amount of the requisite aldehyde in a reaction-inert solvent, such as a lower alkanol containing a small amount of acetic acid, to which is added a catalytic amount of platinum (IV) oxide and the resulting suspension shaken in a hydrogen atmosphere at room temperature for 1–72 hours.

On completion of the reductive amination, the spent catalyst can be filtered and the product isolated by evaporation of the filtrate. Alternately, the reaction suspension can be treated with a mineral acid, such as methanolic hydrogen chloride, the spent catalyst filtered and the product as the hydrochloride salt isolated by evaporation of the filtrate.

The product or its salt can be purified by column chromatography and/or recrystallization from a suitable solvent.

Synthesis of those compounds where $R^1$ is alkyl of one to three carbon atoms is readily achieved by the reaction of I ($R^1$=H) with an appropriate aldehyde or ketone under reductive amination conditions such as those previously described for the preparation of I ($R^1$=H).

Preparation of the requisite amino intermediates can be carried out by the reduction of the corresponding nitro compound or the corresponding phenylazo intermediate as herein described. It may also be convenient not to isolate the amino compound formed by the reduction of the nitro or phenylazo intermediate, but to add the appropriate aldehyde to the completed reaction and continue the reductive amination. The final product I can be isolated and purified as previously noted.

In addition to the use of platinum oxide for the reductive amination reaction, other reducing agents, such as cyano borohydrides disclosed by R. Borch, et al. (J.A.C.S. 93, 2897(1971) can also be employed.

The compounds of the invention form acid additional salts. The pharmaceutically-acceptable acid salts are those formed from acids which form non-toxic acid salts, for example, hydrochloride, hydrobromide, sulfate or bisulfate, phosphate or acid phosphate, acetate, citrate, fumarate, gluconate, lactate, maleate, succinate, tartrate, methanesulfonate, benzenesulfonate, toluenesulfonate, and formate salts.

The pharmaceutically-acceptable salts of the novel compounds of the present invention are readily prepared by contacting said compounds with a stoichiometric amount of an appropriate mineral or organic acid in either aqueous solution or a suitable organic solvent. The salt may then be obtained by precipitation or by evaporation of the solvent.

The compounds of this invention inhibit the activity of the lypoxygenase enzyme. This inhibition has been demonstrated by an assay using rat peritoneal cavity resident cells which determines the effect of said compounds on the metabolism of arachidonic acid.

The compounds of the present invention were tested according to the methods described in Jap. J. Inflammation 7:145–150,1987, "Synthesis of Leukotrienes by Peritoneal Macrophages" for inhibiting lipoxygenase activity.

In this test some preferred compounds indicate low $IC_{50}$ values, in the range of 0.2 to 30 μM, with respect to lipoxygenase inhibition.

The ability of the compounds of the present invention to inhibit lipoxygenase enzyme make them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor, e.g., allergic bronchial asthma, skin disorders, rheumatoid arthritis, osteoarthritis and thrombosis.

Thus, the compounds of the invention and their pharmaceutically acceptable salts are of particular use in the treatment or alleviation of allergic and inflammatory diseases in a human subject.

For treatment of an inflammatory disease such as rheumatoid arthritis the compounds and their pharmaceutically acceptable salts can be administered to a human subject either alone, or preferably, in combination with pharmaceutically acceptable carriers or diluents in a pharmaceutical composition, according to standard pharmaceutical practice.

A compound can be administered a variety conventional routes of administration including orally, parenterally and by inhalation. When the compound is administered orally, the dose range will be from about 0.1 to 20 mg/kg body weight of the subject to be treated per day, preferably from about 0.1 to 1.0 mg/kg per day in single or divided dose. If parenteral administration is desired, then an effective does will be from 0.1 to 1.0 mg/kg body weight of the subject to be treated per day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules, or as an aqueous solution or suspension. In the case of tablets for oral use, carriers which are commonly used include lactose and corn starch. Further, lubricating agents, such as magnesium stearate, are commonly added. In the case of capsules, useful diluents are lactose and dried corn starch. When aqueous .suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions should be suitably adjusted and buffered. For intravenous use, the total concentration of solute should be controlled to make the preparation isotonic.

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows; s, singlet; d, doublet; t, triplet q, quartet, m, multiplet; br, broad.

EXAMPLE 1

5-N-Benzylamino-1,3 dihydro-2,1,3-benzothiadiazole- 2,2-dioxide hydrochloride (Ar=$C_6H_5$; n=1; $R^1$=H;X=H; and Z=—NH)

Platinum oxide (80 mg) was added to a solution of 5-nitro- 1,3-dihydro-2,1,3-benzothiadiazole-2,2-dioxide (1.65 g,7.7 mmol) in 50 ml of methanol containing 0.05 ml of acetic acid and the mixture stirred at room temperature under a hydrogen atmosphere for 4.5 hrs.

Benzaldehyde (850 mg, 8 mmol) was added to the mixture and stirred for 4 hrs under a hydrogen atmosphere. Methanol containing hydrogen chloride (10 ml) was added to the reaction mixture and the spent catalyst was filtered. Removal of the solvent in vacuo gave the crude product which was chromatographed on silica gel (ethyl acetate) and then recrystallized from methanol-diethyl ether, 500 mg., m.p. 193° C. (dec).

NMR (DMSO$d_6$): 4.44(s,2H), 6.8–6.9(br,3H), 7.34–7.40 (m, 3H), 7.47–7.50 (br, 2H) and 11.3 (br, 2H).

EXAMPLES 2–4

Starting with the appropriate reagents and employing the procedure of Example 1, the following compounds were prepared:

6-N-Benzylamino-3H-1,2,3-benzoxathiazoline- 2,2dioxide hydrochloride (Ar=$C_6H_5$; n=1; $R^1$=H; X=H; and Z=O) m.p. 180°–182° C. (dec); NMR(DMSO-$d_6$-$D_2O$) 4.33 (s,2H), 6.57 (d,d,1H,J=8.4, 2 Hz), 6.72 (d,1H,J=2 Hz), 6.83 (d,1H,J=8.4 Hz) and 7.30–7.38 (m,5H).

5-N-Benzylamino-1,3-dihydro-2,1-benzisothiazole-2,2dioxide hydrochloride (Ar=$C_6H_5$; n=1; $R^1$=H; X=H; and Z —$CH_2$—) m.p. 201° C.(dec); NMR (DMSO-$d_6$) 4.43(s,2H), 4.56 (s,2H), 6.85(d,1H, J=8.5 Hz), 7.21(br, 1H), 7.35–7.39(m,4H), 7.40–7.50 (br, 2H) and 10.69 (br, 1H) .

6-N-Benzylamino-3,4-dihydro-1H-2,1-benzothiazine-2,2-dioxide hydrochloride (Ar=$C_6H_5$; n=1; $R^1$=H; X=H and Z=—$CH_2CH_2$—) m.p. 245°–248° C. (dec); NMR (DMSO-$d_6$-$D_2O$) 3.27–3.32 (m,4H), 4.41(s,2H) , 6.76(d, 1H, J=8.4 Hz), 6.98–7.04 (br, 2H) and 7.36–7.45 (m, 5H) .

EXAMPLES 5–7

7-N-Benzylamino-2H, 4H-1,3,4-benzoxathiazine- 3,3-dioxide (Ar=$C_6H_5$; n=1; $R^1$=H; X=H; and Z=—$OCH_2$—).

7-N-Phenylazo-2H, 4H-1,3,4-benzoxathiazine (1.00 g, 3.46 mmol) was dissolved in methanol(50 ml), and hydrogenated with platinum oxide (31 mg) at 1 atm at room temperature. After 4 hours, the starting material was consumed. Benzaldehyde (757 mg, 7.14 mmol) and the additional catalyst (31 mg) were added to the reaction vessel. Hydrogenation was further continued overnight, and the reaction mixture was filtered through Celite. After evaporation of the solvent the residual materials were purified by chromatography (Silica.gel,25% ethyl acetate hexane) and recrystallization from methanol to provide the final product, m.p. 174.6°–176.9° C. (methanol); NMR (DMSO-$d_6$) 4.22(d,5.9 Hz, 2H), 5.01(s,2H), 6.17(d, 2.6 Hz,1H), 6.26–6.34(m,2H), 6.57(d, 8.4 Hz,1H), 7.20–7.33(m,5H) and 9.52(br s,1H) .

In a similar manner 1.04 g of 7-phenylazo-2H,4H- 1,3, 4-benzoxathiazine-3,3-dioxide (3.6 mmol) and 1.0 g of cinnamaldehyde (7.58 mmol) gave 325 mg of 7-N-( 3-phenylpropyl)amino-2H, 4H-1, 3,4-benzoxathiazine- 3,3-dioxide hydrochloride (Ar=$C_6H_5$; n=3; $R^1$=H; X=H; and Z=—$OCH_2$—) m.p. 194°–212.6° C. (methanol); NMR(D-MOS-$d_6$) 1.89(m,2H), 2.67(t, 7.7 Hz,2H), 3.14(t, 7.3 Hz,2H), 5.20(s,2H), 6.80–6.98(m,3H), 7.16–7.32 (m, 5H) and 10.46 (br s, 1H) and 982 mg of 7-phenylazo-2H, 4H-1,3,4-benzoxathiazine-3,3-dioxide (3.4 mmol) and 780 mg of tetrahydropyran-3-carboxaldehyde (6.84mmol) gave 496 mg of 7-N-(tetrahydropyran- 3-yl)methylamino-2H,4H-1,3,4-benzoxathiazine- 3,3-dioxide hydrochloride (Ar=tetrahydropyran-3-yl; n=1;$R^1$=H; X=H; and Z=—$OCH_2$—); m.p. 213° C. (dec); NMR(DMSO-$d_6$) 1.24–1.60(m,3H), 1.83 (m,2H), 2.99(m,2H), 3.14(m, 1H), 3.31(m, 1H) , 5.16 (s, 2H) , 6.79(s, 3H) and 10.29 (br s, 1H).

EXAMPLES 8–9

7-N-Benzylamino-2H, 4H-1,3,4-benzodithiazine- 3,3-dioxide (Ar=$C_6H_5$; n=1; $R^1$=H; X=H; and Z=—$SCH_2$— and 5-N-Benzylamino-2H, 4H-1,3,4-benzodithiazine-3,3-dioxide (Ar=$C_6H_5$; n=1; $R^1$=H; X=H; and Z=—$SCH_2$—)

A mixture of 5- and 7-nitro-2H-1,3,4-benzodithiazine-3,3-dioxide (200 mg) was dissolved in methanol, and platinum oxide (200 mg) was added to it. The prepared solution was hydrogenated at 5 kg/cm$^2$ for 2 days with a Parr shaker. The catalyst was removed by filtration through Celite, and benzaldehyde (1.60 g, 1.51 mmol) and acetic acid (2.0 ml) were dissolved in the filtrate. The resulting mixture was allowed to react with sodium cyanoborohydride (1.0 g, 15.9 mmol) at room temperature for 2 hours. The reaction mixture was concentrated by evaporation, and diluted with ethylacetate. The organic solution was washed with brine, dried over sodium sulfate and concentrated down. The obtained residual oil was subjected to a chromatographic condition (Silica-gel, 20–30% ethylacetate/hexane)Fractions of each two major products were separately collected, and each product was recrystallized from methanol to afford 5N-Benzylamino-2H, 4H- 1,3,4-benzodithiazine-3,3-dioxide (585 mg, less polar fraction), m.p. 115.6°–116.8° C. NMR(DMSO-$d_6$, 270 MHz) 4,33(s,2H), 4.49(s,2H), 6.33 (dd, 1H, 1.8 Hz), 6.49(dd, 1H, 1.8 Hz), 6.86(t,1H, 8 Hz) and 7.22–7.37(m,5H) and the 7-N-benzylamino isomer (655 mg, more polar), m.p. 157.8°–158.9° C. (methanol). NMR(DMSO-$d_6$) 4.22(d,2H 6 Hz), 4.41(s,2H) 6.26(t,1H, 6 Hz), 6.39(d,1H, 2.6 Hz), 6.44(dd, 1H, 2.6 Hz and 8.6 Hz), 6.62(d,1H, 8.6 Hz), 7.20–7.33(m,5H) and 9.53(br s, 1H) .

EXAMPLES 10–15

Starting with requisite materials and employing the reduction-amination procedure of Example 1, the following analogs were prepared:

6-N-Benzylamino-3 -methyl-3,4 -dihydro-1H- 2,1,3- benzothiadiazine-2,2-dioxide hydrochloride (Ar=$C_6H_5$; n=1; $R^1$=H; X=H; and Z=—$CH_2N(CH_3)$—) m.p. 124°–167° C.(dec); NMR(DMSO-$d_6$) 2.58(s,3H) , 4.44(s,2H), 4.53(s, 2H), 6.76(d,1H, J=8.8 Hz), 7.06–7.14(m,2H), 7.32–7.40(m, 3H), 7.45–7.49(m, 2H) and 10.46(br, 1H).

8-N-Benzylamino-3-methyl-3,4-dihydro-1H- 2,1,3-benzothiadiazine-2,2-dioxide hydrochloride (Ar=$C_6H_5$; n= 1; $R^1$=H; X=H; and Z=—$CH_2N(CH_3)$—) m.p. 186.5°–187.5° C.; NMR(DMSO$_{d6}$) 2.64(s,3H) , 4.32(s,2H); 4.49(s,2H), 6.46(br, 2H), 6.88(dd,1H,J=7.7 Hz), 7.23–7.41(m,5H) and 9.28(br,1H).

6-N-Benzylamino-4-methyl-1H-2,1,3-benzothiadiazine, 2,2,-dioxide hydrochloride (Ar=$C_6H_5$; n=1; $R^1$=H; X=H; and Z=—$C(CH_3)$=N—) m.p. 242°–244° C. (dec), NMR(DMSO-$d_6$) 2.53 (s,3H) , 4.37(br,2H), 6.95–6.98(br, 1H) and 7.25–7.44(m,7H).

5-N-Benzylamino-6-fluoro-1,3-dihydro-2,1-benzisothiazole- 2,2-dioxide (Ar=$C_6H_5$; n=1; $R^1$=H; X=F; and Z=—$CH_2$—) m.p. 177°–177.5° C.; NMR(DMSO-$d_6$) 4.29(br, 4H), 5.98(m, 1H), 6.56 (d, 1H,J=8.8 Hz), 6.68 (d, 1H,J=11.7 Hz), 7.21–7.36 (m, 5H) and 9.80(br,1H).

6-N-Benzylamino-3- (pyridin-3-yl )methyl-3,4-dihydro-1H-2,1,3-benzothiadiazine-2,2-dioxide dihydrochloride (Ar=$C_6H_5$; n=1; $R^1$=H; X=H; and Z=—$CH_2N(3$—$C_5H_4NCH_2)$—) m.p. 180° C.(dec); NMR(DMSO-$d_6$) 4.29(s,2H), 4.39(s,2H), 4.63 (s,2H), 6.81(d, 1H,J=8.8 Hz), 7.04(br, 1H), 7.13(br d, 1H, J=7.7 Hz), 7.32–7.51 (m,5H), 8.02 (dd,1H, J=8.1, 5.9 Hz), 8.50(d, 1H,J=8.4 Hz), 8.85–8.86(m,2H) and 10.81(br,1H.

6-N-Benzylamino-3,4-dihydro-1H-2,1,3-benzothiadiazine- 2,2-dioxide (Ar=$C_6H_5$; n=1; $R^1$=H; X=H; and Z=—$CH_2NH$—) m.p. 185.5°–186.5° C., NMR(DMSO-$d_6$) 4.19– 4.25(m,4H), 5.97(t,1H,J=6.2 Hz) , 6.34(br,1H), 6.47(br,2H), 6.98(t,1H,J=7 Hz), 7.18–7.36(m,5H) and 9.33 (br, 1H).

EXAMPLES 16–17

7-N- (Tetrahydropyran-3-ylmethyl)amino-2H, 4H- 1,3,4-benzodithiazine-3,3-dioxide hydrochloride (Ar=$3C_5H_9O$; n=1; $R^1$=H; X=H; and Z=—S—$CH_2$).

Iron powder (4.0 g, 71.6 mmol) was added in several portions to the suspension of a mixture of 7- and 5-nitro-2H, 4H-1,3,4-benzodithiazine-3,3-dioxide (c.a. 3:1 mixture, 4.00 g, 16.3 mmol) in methanol (150 ml) and conc. HCl (25 ml) chilled in an ice-bath, and the mixture was heated at reflux for 1 hour. The reaction mixture was filtered through filtering paper, and the filtrate was discarded. The remaining insoluble materials were washed with hot methanol several times, and the methanol filtrate was concentrated. Ether was added to the methanolic residue, and the formed solids were collected by filtration to afford 7-amino-2H, 4H-1,3,4-benzodithiazine-3,3-dioxide hydrochloride (2.29 g, 56%) without contamination of the 5-amino isomer.

To the suspension of 7-amino-2H,4H-1,3,4-benzodithiazine- 3,3-dioxide (713 mg, 3.31 mmol) in methanol (40 ml) were added tetrahydropyran-3-yl-carbaldehyde (377 mg, 3.31 mmol) and acetic acid (0.4 ml) at room temperature. Sodium cyanoborohydride (190 mg, 3.02 mmol) was added and the resulting mixture was stirred overnight. The solvent was removed by evaporation, and the residue was basified with aqueous sodium bicarbonate. The resulting mixture was extracted with ethylacetate. The organic extracts were washed with brine, dried over magnesium sulfate, and concentrated down. The obtained oil was treated with methanolic hydrogen chloride, and evaporated down to yield the hydrochloride-salt, which was recrystallized from methanol to afford 613 mg of the desired product, m.p. 230°–242° C. (dec). NMR(DMSO-$d_6$) 1.19–1.65 (m, 3H), 2.78–2.96 (br m, 2H), 2.99 (m, 2H), 3.14 (m, 1H), 3.32(m, 1H), 3.70(dm, 1H,J=11 Hz), 3.86(br d, 1H,J=11 Hz), 4.54(s, 2H), 6.82(d,1H,J=8.4 Hz), 6.97(br m, 2H) and 10.24(br s, 1H).

In a similar manner 720 mg of 7-amino-2H,4H- 1,3,4-benzodithiazine-3,3-dioxide hydrochloride (2.85 mmol) and 479 mg of 3-(pyridin-3-yl)propanal (3.55 mmol) gave 762 mg of 7-N-[3-(pyridin-3-yl)propyl]amino-2H,4H- 1,3,4-benzodithiazine-3,3-dioxide dihydrochloride (Ar=$C_5H_4N$; n=3; $R^1$=H; X=H; and Z —$SCH_2$—) m.p. 241.8°–243.9° C. (dec). NMR(DMSO-$d_6$), 2.50(m,2H), 2.92(t,2H,J=7.7 Hz), 3.14(t,2H,J=6.8 Hz), 4.56(s, 2H), 6.83(d, 1H,J=8.4 Hz), 7.00–7.06(br m, 2H), 8.01(dd,2H,J=6.8 Hz), 8.51(d, 1H,J=8 Hz), 8.79(d, 1H,J=6 Hz), 8.87(s,1H) and 10.36(br s, 1H).

EXAMPLE 18

7-N- [3-(Oxazol-5-yl)propyl]amino-2H, 4H- 1,3,4-benzodithiazine-3,3-dioxide hydrochloride (Ar=$C_3H_2NO$; n=3; $R^1$=H; X=H; and Z=—$SCH_2$—)

Employing the procedure of Example 16/17 700 mg of 7-amino-2H, 4H-1,3,4-benzodithiazine-3,3-dioxide hydrochloride (2.77 mmol), and 370 mg of 3-(oxazol-5yl)propanal (2.96 mmol) gave 505 mg of the title product m.p. 211°–220.5° C.(dec) NMR(DMSO-$d_6$) 2.50(m,2H), 2.78(t, 2H,J=7 Hz), 3.19(t,2H,J=7 Hz), 4.58(s,2H), 6.86(d, 1H,j=9 Hz), 6.93(s,1H), 7.03–7.13(m,2H), 8.23(s,1H) and 10.44 (br s, 1H).

EXAMPLES 19–20

7- [3- (3-Pyridyl)prolamino]-2H 4H-1,3,4-benzoxa-thiazine- 3,3-dioxide (Ar=—$C_5H_4N$; n=3; $R^1$H; X=H; and Z=—$OCH_2$—)

Using the reducing procedure of Example 5, 1.0 g (3.5 mmol) of 7-phenyldiazo-2H, 4H-1,3,4-benzoxathiazine-3,3-dioxide was reduced to the corresponding 7-amino compound and coupled with 1.0 g (8.5 mmol) of 3- (3-pyridyl)propanal using the procedure of Example 8 to give 220 mg of the titled product, m.p. 163°–164° C. NMR(DMSO-$d_6$) 1.81(q,2H,J=3 Hz), 2.68(t,2H,J=3 Hz), 2.01–3.01(m,2H), 5.03(s,2H), 5.66(br,1H), 6.18(d,1H,J=2 Hz), 6.29(dd,1H,J=2 and 9 Hz) 6.60(d,1H,J=9 Hz) 7.31(dd,1H,J=5 and 8 Hz) 7.64(dt,1H,J=8 Hz), 8.40(dd,1H,J=2 and 5 Hz), 8.45(d,1H, J=2 Hz), 9.51(br,1H).

In a similar manner was prepared 7-[3-( 5oxazolyl)propylamino]2H, 4H-1,3,4-benzoxathiazine- 3,3 -dioxide hydrochloride (Ar=$C_3H_2NO$; n=3; $R^1$50 H; X=H; and Z= —$OCH_2$—), m.p. 190°–193° C. NMR(DMSO-$d_6$) 1.95(q2H,J=7 Hz), 2.79(t,2H,J=7 Hz), 3.23(t,2H,J=7 Hz), 5.24(s,2H), 6.87–6.95(m,2H), 7.09(br,2H), 8.24(s,1H), 10.70(br,1H)

EXAMPLE 21

6-N-Benzylamino-4-oxo-3,4-dihydro-1H- 2,1-benzothiazine-2,2-dioxide (Ar=$C_6H_5$; n=1; $R^1$=H X=H; X=H; and Z=—C(O)$CH_2$—)

Following the procedure of Example 1, 460 mg (2.2 mmol) of 6-nitro-4-oxo-3,4-dihydro-1H-2,1-benzothiazine2,2-dioxide (obtained by the nitration of 4-oxo- 3,4-dihydro-1H-2,1-benzothiazine-2,2-dioxide) was coupled with 240 mg (2.2 mmol) of benzaldehyde to give 150 mg of the titled product, m.p. 172°–173° C. NMR(DMSO-$d_6$) 4.28(d,2H,J=6 Hz), 4.56(s,2H), 6.45(br,1H), 6.84–6.88(m, 1H), 6.97–7.02(m,2H), 7.18–7.38(m,5H) and 10.78(br,1H)

PREPARATION A

3-Methyl-6- and 8-nitro-3,4-dihydro-1H-
2,1,3-benzothidiazine-2,2-dioxide 1. 2-Amino-N-methyl-benylamine O-Nitro-benzaldehyde (20 g: 132mmol) was dissolved in chloroform (60 ml). Methylamine (40% methanol solution; 60 ml) was added at room temperature, and the mixture was stirred for 12 hours. Sodium borohydride (5.8 g) was added portionwise to the reaction mixture and stirred for 5 hours, then water (100 ml) was added and extracted with chloroform.

Extract was dried over magnesium sulfate and solvent was removed in vacuo. Crude product was purified by column chromatography on silica gel (Hexane ethyl acetate=1:2).

Product was dissolved in ethanol(50 ml). 5%-Pd/C (0.5 g) was added, and mixture was stirred for 4.5 hours under hydrogen atmosphere at room temperature. The catalyst was filtered off and solvent was removed in vacuo. Crude product was distilled Kugel rohr (200° C./3 mm Hg; atmosphere temp.) to give the product (3.8 g).

2. 3-Methyl-3,4-dihydro-1H-2,1,3-benzothiadiazine- 2,2dioxide

2-Amino-N-methyl-benzylamine (3.7 g;27mmol) and sulfamide (5.2 g: 54 mmol) were dissolved in pyridine (40 ml). Mixture was refluxed for 3 hours, then the solvent was removed in vacuo, and water (50 ml) was added. Reaction mixture was extracted with ethyl acetate. Extract was dried over magnesium sulfate and solvent was evaporated off. Crude product was recrystallized from chloroform-hexane, to give the product, (4.4 g).

3. 3-Methyl-6-and 8-nitro3,4-dihydro-1H-2,1,3- benzothiadiazine- 2,2-dioxide

3-Methyl-3,4-dihydro-1 H-2,1,3-benzothiadiazine- 2,2dioxide was added to 70% nitric acid at (50 ml) 0° C. Mixture was stirred for 1 hour at same temperature then poured into ice-water mixture.

The reaction mixture was extracted with ethyl acetate and washed with water. Extract was dried over magnesium sulfate, and solvent was removed under reduced pressure Diethyl ether (20 ml) was added to the crude product. Precipitate was collected by filtration, to give 3-Methyl-8- nitro-3,4-dihydro-1H-2,1,3-benzothiadiazine-2,2-dioxide (0.64 g).

Filtrate was purified by column chromatography on silica gel(Hexane-ethyl acetate =3;1 ), to give 3-Methyl6-nitro-3,4-dihydro-1H-2,1,3-benzothiadiazine-2,2-dioxide (1.7 g).

PREPARATION B

6-Nitro-4-methyl-1H-2,1,3-benzothiadiazine-2,2-dioxide

Sulfuric Acid (98%) (15 ml) was added portionwise to cooled (0° C.) 70% Nitric acid (15 ml). Mixture was cooled to −5° C. then 4-Methyl-1H-2,1,3-benzothiadiazine- 2,2-dioxide[a], (1.8g) was added and stirred for 5 minutes. Reaction mixture was poured into ice-water mixture and extracted with ethyl acetate. Extract was dried and solvent removed in vacuo to give the crude product which was used without further purification. [a]JP (Kokoku)-4359 (1968)

PREPARATION C

6-Nitro-3H-1,2,3-benzoxathiazoline-2,2-dioxide

Diethylene glycol dimethyl ether (350 ml) solution of 2-Amino-5-Nitrophenol (40 g) and sulfamide (25 g) was added dropwise to refluxing diethylene glycol dimethyl ether (100 ml) over a period of 50 minutes. Mixture was stirred and refluxing continued 15 minutes, then cooled to room temperature. Solvent was evaporated off, and 500 ml of 1N hydrochloric acid was added. Reaction mixture was extracted with diethyl ether, extract was dried over magnesium sulfate and solvent was removed in vacuo. Crude product was purified by the column chromatography on silica gel (2% Methanol-Ethyl acetate) to give the desired intermediate, 10.5 g.

PREPARATION D 2H,4H-1,3,4-Benzoxathiazine-3,3-dioxide 1. 2-(chloromethylsulfonylamino)Phenol O-Aminophenol (43.6 g, 0.40 mol) was dissolved in tetrahydrofuran (200 ml). Chloromethanesulfonyl chloride (61.8 g, 0,415 mol) was slowly added to the solution at room temperature, and the resultant solution, was stirred for 30 minutes. Pyridine (45 ml) was added to the solution, and stirring was continued overnight. The reaction mixture was acidified to pH=1 with hydrochloric acid and extracted with ethyl acetate. The organic extracts were washed with sodium bicarbonate aq. and brine followed by drying over sodium sulfate. The solvent was removed by evaporation, and the residual oil was sitting at room temperature for 2 days to form crystals, which were collected by filtration to afford the titled product, 18.5 g.

2H,4H-1,3,4-benzoxathiazine-3,3-dioxide

The above sulfonamido (18.5 g, 83.7 mmol) and potassium carbonate (35.5 g, 257 mmol) were mixed with methanol (90 ml), and the resulting suspension was heated at reflux for 1.5 hours. The reaction mixture was acidified to pH=1 with hydrochloric acid. The solvent (methanol) was removed by evaporation. The formed solids were collected by filtration to afford the titled product which was purified by recrystallization from isopropanolether to yield a pure product, m.p. 120.8°–124.8° C.

PREPARATION E

7-Phenylazo-2H,4H-1,3,4-benzoxathiazine-3,3 dioxide

Aniline (6.40 g, 68.8 mmol) was dissolved in a mixture of water (50 ml) and hydrochloric acid (20.5 ml, 246 mmol). The aniline solution was chilled in an ice-bath, and a solution of sodium nitrate (5.0 g, 58.8 mmol) in water (10 ml) was added to it to afford a yellow solution. 2H,4H-1,3, 4-Benzoxathiazine-3,3-dioxide (4.0 g, 21.6 mmol) and potassium carbonate (12.5 g, 90.6 mmol) were mixed together in methanol (50 ml). To the resultant suspension chilled in ice-bath was added 37% by volume of the above yellow solution. The reaction mixture was acidified to pH=1 with diluted hydrochloric acid. The formed red solids were collected by filtration and dried under vacuum to afford the titled compound, 3.5 g.

PREPARATION F 2H,4H-1,3,4-benzodithiazine-3,3-dioxide

Chloromethanesulfonyl chloride (61.8 g, 415 mmol) was slowly added to a cold solution of 2-aminophenyl disulfide (48.0 g, 193 mmol) in pyridine (200 ml) chilled in an ice bath. The resultant solution was stirred at room temperature for 2 hours, and heated at 60° C. for 30 minutes. The reaction mixture was concentrated by evaporation, acidified to pH=1 with diluted hydrochloric acid and extracted with ethyl acetate. The extracts were washed with aqueous sodium bicarbonate and brine, and dried over sodium sulfate. Evaporation of the solvents provided a crude chloromethanesulfonamide, which was used for the next reaction without further purification.

Sodium borohydride (7.5 g, 198 mmol) was slowly added in several portions to the crude sulfonamide dissolved in methanol (400 ml). The resultant mixture was heated at reflux for 1 hour. Additional sodium borohydride (3.6 g, 95 mmol) was added, and heating was continued further. After 1 hour, the reaction mixture was concentrated by evaporation, and acidified to pH=1 with diluted hydrochloric acid to afford solids, which were clashed by sonication, and collected by filtration. The crude product was recrystallized from toluene containing trace amounts of methanol to provide pure 2H,4H-1,3,4-benzodithiazine- 3,3-dioxide (35.36 g, 46% yield).

PREPARATION G 5- and 7-Nitro,2H,4H-1,3,4-benzodithiazine-3,3-dioxide

A finely ground 2H,4H-1,3,4-benzodithiazine-3,3dioxide (3.00 g, 14.9 mmol) was added in several portions to a well chilled 70% nitric acid (180 ml) in an ice-methanol-dry ice bath. The interval of addition was adjusted for keeping the inner temperature around −10° C. After addition was completed, the resultant mixture was poured into ice-water (600 ml). A small amount of insoluble materials was removed by filtration, and the filtrate was extracted with methylene chloride. The extracts were washed with brine, dried over sodium sulfate, and concentrated down to provide a mixture of 5-and 7-nitro-2H,4H-1,3,4-benzodithiazine-3,3-dioxide.

PREPARATION M

7-Amino-2H,4H-1,3,4-benzodithiazine-3,3-dioxide

7-Nitro-2H,4H-1,3,4-benzodithiazine-3,3-dioxide was dissolved in methanol (200 ml) and $PtO_2$ (200 mg) was added to it. The prepared solution was hydrogenated at 5 kg/cm$_2$ for 2 days with a Parr shaker to afford 7-amino-2H, 4H-1,3,4-benzodithiazine-3,3-dioxide, m.p. 184°–193° C.

PREPARATION I

5-Nitro-1,3-dihydro-6-fluoro-2,1-benzisothiazole-2,2-dioxide 1. 4-fluoro-2-nitrobenzyl bromide To a stirred solution of 4-fluoro-2-nitro toluene (48.9 g) and N-bromosuccinimide (56 g) in carbon tetrachloride (300 ml) was added benzoylperoxide (0.78 g). The mixture was heated under reflux for 90 minutes. Additionally, benzoylperoxide (0.78 g) was added to the mixture. Reflux was continued 90 minutes then, cooled to room temperature.

The reaction mixture was filtered and the precipitate was washed with carbontetrachloride. The filtrate was concentrated in vacuo The crude product was distilled under reduced pressure (102°–107° C./0.9–2.5 mmHg) to afford the titled product, 50.3 g 2. Sodium 4-fluoro-2-nitrobenzylsulfonate A solution of 4-fluoro-2-nitrobenzylbromide (50.1 g) and sodium sulfite (27.3 g) in water (200 ml) was heated under reflux for 2.5 hours and cooled to room temperature. The solvent was removed under reduced pressure and ethanol (100 ml) was added to the crude product.

The product was isolated by filtration, to give the product (53.8 g).

3. Sodium 2-amino-4-fluorobenzylsulfonate

To a stirred suspension of sodium 4-fluoro- 2-nitrobenzylsulfonate (51.12 g) in $H_2O$ (450 ml) was added $PtO_2$ (1.0 g) and 0.5N-sodium hydroxide solution (2 ml). The mixture was stirred under $H_2$ atmosphere for 24 hours. The catalyst was renewed and the mixture was stirred under $H_2$ atmosphere for 24 hours.

The catalyst was filtered off and the filtrate was concentrated in vacuo. The crude product was recrystallized from methanol diethyl ether to give sodium 2-amino-4-fluorobenzylsulfonate (18.7 g).

4. 1,3-dihydro-6-fluoro-2,1-benzisothiazole-2,2-dioxide 2-amino-4-fluorobenzylsulfonate (11.0 g) was added to phosphorous oxychloride (100 ml) at 50° C. and the mixture was heated under reflux for 6 hours. The reaction mixture was concentrated in vacuo and the resulting grease was poured into ice-water mixture. A sodium hydroxide solution was added to the mixture at 0° C. until the mixture was basic. Insoluble material was filtered off and washed with water. The filtrate was treated with aqueous hydrochloric acid solution (pH=2.5). The crude product was separated by filtration. Ethyl acetate was added to the precipitate and the insoluble material was filtered off. The filtrate was concentrated in vacuo, to give 1,3-dihydro- 6-fluoro-2,1-benzisothiazole 2,2-dioxide (3.2 g)

5. 1-ethoxycarbonyl-1,3-dihydro-6-fluoro-2,1benzisothiazole2,2-dioxide

To a stirred solution of 1,3-dihydro-6-fluoro-2,1-benzisothiazole- 2,2-dioxide (2.57 g) in anhydrous pyridine (8 ml) was added ethyl chloroformate (1.79 g) at 0° C. under $N_2$ atmosphere. The mixture was stirred for 30 minutes and concentrated in vacuo. Cold hydrochloric acid was added to the precipitate (pH=6). The resulting solution was extracted with ethyl acetate. The organic layer was washed with water and dried over magnesium sulfate. The crude product was purified by silica gel column chromatography (methylene chloride-ethyl acetate 95:5) to give 1-ethoxycarbonyl-1,3-dihydro-6-fluoro- 2,1-benzisothiazole 2,2-dioxide (3.1 g).

6. 5-nitro-1-ethoxycarbonyl-1,3-dihydro-6-fluoro- 2,1-benzisothiazole-2,2-dioxide To stirred nitric acid (99%; 25 ml) was added 1-ethoxycarbonyl- 1,3-dihydro-6-fluoro-2,1-benzisothiazole 2,2-dioxide (2.78 g) in portions at 0° C. The mixture was stirred for 2 hours while allowing it to warm to 10° C. The reaction mixture was poured into ice-water mixture then, the resulting mixture was extracted with ethyl acetate. The organic layer was washed with saturated sodium bicarbonate solution. The extract was dried over magnesium sulfate and concentrated in vacuo. The resulting crude product was washed with methanol, to give 5-nitro-1-ethoxycarbonyl-1, 3-dihydro-6-fluoro-2,1-benzisothiazole 2,2-dioxide (3.11 g).

7. 5-nitro-1,3-dihydro-6-fluoro-2,1-benzisothiazole 2,2dioxide

Into a stirred solution of 5-nitro-1-ethoxycarbonyl-1,3-dihydro-6-fluoro-2,1-benzisothiazole-2,2-dioxide (3.11 g) in ethanol (75 ml) was bubbled ammonia gas for 3 hours under reflux condition. The reaction mixture was cooled to room temperature and the solvent was removed under reduced pressure. Dilute hydrochloric acid solution was added to a precipitate (pH<7) and the mixture was extracted with ethyl acetate. The extract was dried over magnesium sulfate and concentrated in vacuo. The crude product was purified by silica gel column chromatography (1%-methanol-ethyl acetate) to give 5-nitro-1,3-dihydro- 6-fluoro-2,1-benzisothiazole 2,2-dioxide (0.94 g).

We claim:

1. A compound of the formula

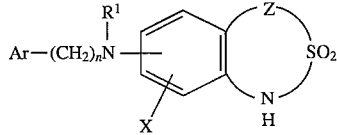

and the pharmaceutically acceptable acid addition salts thereof, wherein Ar is cycloalkyl having five to seven carbon atoms, tetrahydropyranyl, pyridyl, oxazolyl, phenyl or substituted phenyl wherein said substituent is methyl, methoxy, fluoro, chloro or trifluoromethyl; n is an integer of 1 to 3; X is hydrogen, methyl, methoxy, fluoro, chloro or trifluoromethyl; Z is —NH— or —O—; and $R^1$ is hydrogen or alkyl having one to three carbon atoms.

2. A compound of claim 1, wherein Ar is tetrahydropyranyl; n is 1; and $R^1$ is hydrogen.

3. A method for treating an allergic or inflammatory condition in a mammal which comprises administering to said mammal an antiallergy or antiinflammatory effective amount of a compound according to claim 1.

4. A pharmaceutical composition for the treatment of allergic or inflammatory conditions in a mammal, said composition comprising an effective amount of a compound according to claim 1 with a pharmaceutically acceptable carrier.

* * * * *